United States Patent [19]

Kilmon

[11] Patent Number: 4,672,107

[45] Date of Patent: Jun. 9, 1987

[54] CELL GROWTH INHIBITOR AND METHOD

[75] Inventor: Jack Kilmon, Houston, Tex.

[73] Assignee: Inbex, Inc., Houston, Tex.

[21] Appl. No.: 723,614

[22] Filed: Apr. 15, 1985

[51] Int. Cl.$^4$ ............................................. C07K 15/00
[52] U.S. Cl. ................................................... 530/350
[58] Field of Search .............. 260/112.5 K; 530/300, 530/324, 350

[56] References Cited

U.S. PATENT DOCUMENTS 3,888,977  6/1975  Sanders .................................. 424/98

OTHER PUBLICATIONS

Federation Proceedings, vol. 40, 1981, Abstract 230.
Ewell, et al., Federation Proceedings, vol. 40, No. 6 (1981).
Miller, P. G., "Can Cobras Cure Cancer?", Argosy, pp. 32–37, Oct. 1976.
Collier, R. J. et al., "Immunotoxins," Scientific American, pp. 56–64, Jul. 1984.
Kilmon, J. A., "High Tolerance to Snake Venom by the Virginia Opossum, *Didelphis Virginiana*," Toxicon, vol. 14, pp. 337–340 (1976).
Price, J., "Man Believes Opossums a Cancer Key," The News American, Oct. 12, 1977.
Zaheer, A. et al., "Comparative Study of Three Basic Polypeptides from Snake Venoms in Relation to Their Effects on the Cell Membrane of Normal and Tumor Cells," Cancer Biochem. Biophys., vol. 5, pp. 41–46 (1980).
Man, D. P. et al., "Purification, Characterization and Analysis of the Mechanism of Action of Four Anti-Complementary Factors in Crotalus Atrox Venom," Immunochemistry, vol. 14, pp. 521–527 (1977).
Tu, A. T. et al., "Cytotoxic Effects of Snake Venoms on KB and Yoshida Sarcoma Cells," Research Communications in Chemical Pathology and Pharmacology, vol. 9, No. 4, pp. 783–786 (Dec. 1974).

*Primary Examiner*—Delbert R. Phillips
*Attorney, Agent, or Firm*—Pravel, Gambrell, Hewitt & Kimball

[57] ABSTRACT

A cell growth inhibitor consisting essentially of a peptide substantially free of cytotoxins and containing an amino acid sequence of Phe-Cys-Arg-Phe-Leu-Leu-Cys-Pro-Ser-Arg-Thr-Ser-Asp. The peptide may be obtained by fractionation of venom from proteroglyphodont snakes. One cytostatically active fraction contains a peptide with a molecular weight of 3200–3500 daltons, 27–29 amino acid groups, and a blocked amino terminus. Another fraction contains an oligomer or precursor of the lower molecular weight peptide. Also disclosed is a method of inhibiting the growth of cells by introducing the cell growth inhibitor to the cells to be inhibited in an effective amount.

17 Claims, No Drawings

CELL GROWTH INHIBITOR AND METHOD

FIELD OF THE INVENTION

The present invention relates to the discovery of a cytostatic peptide obtained from poisonous snake venom, and particularly, to such a peptide which has substantial activity as a cell growth inhibitor and is substantially free of cytotoxins.

BACKGROUND OF THE INVENTION

Routine centrifugation of pooled snake venoms reveals significant yields of sloughed secretory epithelia. This cell loss results from the fact that synthesis and secretion of venom on the cellular level is a very high energy absorbing process. Gennaro, J. F., *Anatomical Records*, vol. 136, p. 196 (1960). The secretory epithelia therefore "burn out" at a very rapid rate and require proliferative replacement at rates in excess of normal cell lines. This excess proliferation is believed to be stimulated by a snake venom growth factor (SVGF) that exists in the venom. *Federation Proceedings*, vol. 40:6 (1981). One of the most potent growth factors known is Epidermal Growth Factor (EGF) that stimulates the incorporation of $^3$[H]-thymidine into the newly synthesized DNA of human embryonic palatal mesenchymal cells by a little more than twofold. Yoneda, T. and Pratt, R. M., *Science*, vol. 213, pp. 563–565 (1981). Since the snake venom growth factor (SVGF mentioned above has been observed to increase the incorporation of $^3$[H]-thymidine into the DNA of Vero cells by elevenfold, SVGF is believed to be a more potent growth factor than EGF.

SUMMARY OF THE INVENTION

It has been discovered that there exists a non-toxic fraction in snake venom which is believed to function as a homeostatic regulator that returns the proliferative secretory epithelial snake cells to quiescence. The fraction can be substantially separated from toxic substances occurring in the venom, and the separated fraction exhibits substantial utility as a cell growth inhibitor.

In one aspect, the invention provides a cell growth inhibitor which consists essentially of a peptide substantially free of cytotoxins. The peptide contains an amino acid sequence of Phe-Cys-Arg-Phe-Leu-Leu-Cys-Pro-Ser-Arg-Thr-Ser-Asp and preferably, contains about 27–29 amino acid groups and a blocked amino terminus, and has a molecular weight of about 3200–3500 daltons.

In another aspect, the invention provides a cell growth inhibitor which is essentially a fraction of venom, venom secretory epithelia, or any combination of venom and venom secretory epithelia from a species of proteroglyphodont venomous snake. The fraction is substantially free of toxic substances occurring in the venom and the venom secretory epithelia, and contains an acid and heat stable peptide exhibiting substantial utility as a cell growth inhibitor. The fraction is preferably obtained by a method which includes the steps of (a) separating an acid-soluble, heat stable portion from the venom, the venom secretory epithelia, or a combination thereof, and (b) separating the peptide-containing fraction from the acid soluble portion by dialysis, gel filtration chromatography, high pressure liquid chromatography, electrophoresis, electrofocusing chromatography, ion exchange chromatography or a combination thereof.

In yet another aspect, the invention provides a method of inhibiting cell growth, including the step of introducing to the cells to be inhibited a peptide substantially free of cytotoxins and containing an amino acid sequence of Phe-Cys-Arg-Phe-Leu-Leu-Cys-Pro-Ser-Arg-Thr-Ser-Asp. The peptide preferably contains about 27–29 amino acid groups and a blocked amino terminus, and has a molecular weight of about 3200–3500 daltons. The peptide is also preferably obtained by fractionation of venom, venom secretory epithelia, or a combination thereof, from a proteroglyphodont venomous snake.

DETAILED DESCRIPTION OF THE INVENTION

The cell growth inhibitor consists essentially of a peptide having the partial amino acid sequence of Phe-Cys-Arg-Phe-Leu-Leu-Cys-Pro-Ser-Arg-Thr-Ser-Asp. For convenience, this sequence is referred to herein as "FCRFLLCPSRTSD". It is believed that any peptide having the partial amino acid sequence FCRFLLCPSRTSD exhibits substantial utility as a cell growth inhibitor, regardless of whether it is synthesized or derived from natural sources. By the term "cell growth inhibitor" is meant a substance the presence of which produces a substantial cytostatic effect on cells, such as is indicated, for example, by a marked reduction of $^3$[H]-thymidine uptake on incubation.

Preferably, the peptide contains about 27–29 amino acid groups and a blocked amino terminus, and has a molecular weight of about 3200–3500 daltons, although cytostatically active larger peptide precursors and oligomers are also contemplated. In addition, the peptide is preferably acid soluble and stable, and heat stable.

The cell growth inhibitor may be obtained essentially as a fraction of venom, venom secretory epithelia homogenate, or a combination of venom and venom secretory epithelia homogenate, hereinafter collectively referred to as "venom", from any species of proteroglyphodont venomous snake. Because the fraction obtained is believed to be more cytostatic and to occur in a greater relative proportion, the cell growth inhibitor is preferably obtained from the venom of a species of Sistrurus or Crotalus (rattlesnakes), particularly the species *Crotalus atrox* (Western Diamondback Rattlesnake).

The cytostatically active venom fraction may be obtained by first substantially separating the acid-soluble, heat stable portion from the venom, and then substantially separating the peptide-containing fraction from the acid-soluble, heat stable portion by dialysis, gel filtration chromatography, electrophoresis, electrofocusing, high pressure liquid chromatography, ion exchange chromatography or a combination thereof The acid-soluble, heat stable portion is preferably separated from lyophilized whole venom, although fresh or fresh frozen venom may also be used. The venom is reconstituted in a suitable acidic medium, such as, for example, a solution of 0.1–10M acetic acid or the like in water or a suitable organic solvent. The insoluble portion can then be removed by filtration, centrifugation or the like, preferably by centrifugation, and the acid-soluble portion recovered. Typically, reconstitution of 250 mg lyophilized venom in about 10 ml of 1M acetic acid in water with stirring for one hour centrifuging the reconstituted mixture at 10,000 g's for 2 hours, and collecting the supernatant liquid is adequate for this purpose.

Optionally, the venom or the acid soluble portion thereof may be heated to a temperature and for a period of time sufficient to substantially react heat instable substances therein.

A fraction containing the cytostatically active peptide is then separated from the acid-soluble portion by dialysis, gel filtration chromatography, electrophoresis, electrofocusing, high pressure liquid chromatography, ion exchange chromatography, or similar separation techniques, or by a combination of these techniques. Preferably, the acid-soluble portion is first dialyzed to remove very low molecular weight substances, e.g., substances with molecular weights below about 1000 daltons, and then separated into fractions substantially according to molecular weight by gel filtration chromatography. Then, if desired, the cytostatically active fraction obtained by the gel filtration chromatography may be, and preferably is, further purified by high pressure liquid chromatography.

The dialysis of the acid-soluble portion of the venom may be effected by placing the acid-soluble venom portion in a dialysis sack made of a semipermeable material and dialyzing against a suitable solvent which preferably has substantially the same constitution as the liquid medium in which the venom was reconstituted. Typically, dialysis in a cellophane dialysis sack against 1M aqueous acetic acid for a period of about 12 hours with dialyzate replacement at 4 and 8 hours is adequate to substantially remove substances with molecular weights below about 1000 daltons, although similar techniques which effect about the same degree of separation are also suitable.

The dialyzed portion, i.e., the portion not passing through the semipermeable membrane, is then separated by gel filtration chromatography or a similar technique into a plurality of fractions according to relative molecular weights. Typically, the gel filtration chromatographic column is packed with polyacrylamide gel, polysaccharide gel, or the like, and a sample of the dialyzed acid-soluble venom portion is placed in the column and eluted therethrough with a carrier at a predetermined flow rate. The carrier may be any suitable solvent, such as water or an organic solvent and preferably has the same constitution as the liquid medium in which the venom was reconstituted and the acid soluble portion thereof dialyzed against. The fractions are collected as eluate at predetermined intervals, or as indicated by an eluate detector, such as, for example, a spectrophotometer, preferably monitoring at about 280 nm. Preferably, each fraction obtained by the gel filtration chromatography contains venom components with molecular weight variances of about 200-500 daltons or less. Also contemplated are similar separation techniques which provide substantially equivalent resolution of the venom into fractions according to molecular weight, such as, for example, electrophoresis, electrofocusing or the like.

If the elution time of the cytostatically active peptide is not known, each fraction of collected eluate is introduced into a culture which is then incubated, and the fraction containing the cytostatically active peptide is identified by observing the relative growth rates of the cultures. The growth rate of the cultures is conveniently determined, for example, by assaying the cultures for $^3[H]$-thymidine incorporation into newly formed DNA. Once the cytostatocally active fraction is identified, the elution time thereof can be readily determined. Thereafter, if a new or different gel filtration column is used, or if the gel filtration conditions are changed, a sample of the previously collected fraction can be used to readily determine the elution time of the desired peptide-containing venom fraction.

With sufficient resolution by gel filtration to substantially remove cytotoxic substances, the fraction containing the cystostatically active peptide may be used in its crude form as a cell growth inhibitor, but may also be, and preferably is, further purified to substantially remove cytostatically inactive substances as well. Preferably, the cytostatically active fraction is further purified by high pressure liquid chromatography (HPLC) by elution with a suitable solvent through a suitable packed chromatograph column. For example, elution with about 0.05 wt. % aqueous trifluoroacetic acid with a gradient of acetonitrile, initially at 0 wt. % and gradually increased to about 60 wt. % of the elution solvent, through a column such as $\mu$-bonde-pak C18 obtained from Waters Associates, Houston, Tex., is suitable for this purpose, although similar HPLC techniques or the like are also contemplated.

The cell growth inhibitor of the present invention is a particularly effective cytostatic agent. Since it is substantially free of cytotoxins, the cell growth inhibitor can be used to inhibit the growth of cells by introducing an effective amount of the cell growth inhibitor to the cells to be controlled. Cells amenable to such growth inhibition include in vitro cultured cell lines. Further, it is contemplated that the growth of cells may be inhibited in vivo in animals such as mammalia, including human, since it is substantially free of cytotoxins.

It is further believed that the growth inhibitor and the method of the present invention has utility as an anti-tumor and tumoristatic agent in the treatment of a wide variety of benign and malignant neoplasms, such as carcinomas, melanomas, sarcomas, and leukemias. Generally, introduction to the cells to be treated of about 50 ng of the cytostatically active peptide is sufficient to arrest the proliferations of at least about 100,000 melanoma cells. The cell growth inhibitor may be introduced to the target cells by direct injection at the primary site, or by oral or intravenous administration if the cytostatic peptide is conjugated with a tumor-specific antibody.

The preparation and utility of the cell growth inhibitor is demonstrated by way of the examples which follow.

Venom Fractionation

The cell growth inhibitor was obtained from lyophilized whole venom of *Crotalus atrox* (Western Diamondback Rattlesnake). A 250 mg sample of the lyophilized whole venom was reconstituted in 10 ml 1M aqueous acetic acid at 4° C. with stirring for about 1 hour. The mixture was then centrifuged at 10,000 g's for 2 hours. The supernatant liquid was placed in a cellophane dialysis sack and dialyzed against 2000 ml of 1M acetic acid while continuously stirring, with dialyzate replacement at 4 and 8 hours.

A gel filtration chromatographic column was prepared by first dissolving polyacrylamide gel (obtained from Bio-Rad Laboratories, Inc., Richmond, Calif. under the designation Bio-Gel P100) in 1M aqueous acetic acid and degassing under vacuum. The gel was packed into a column measuring 100 cm long by 2.5 cm in diameter. The column was calibrated with 5 mg each of Bovine insulin (6,000 daltons), cytochrome C (12,500 daltons) and Bovine serum albumin (67,000 daltons), mixed together in 5 ml of 1M aqueous acetic acid, added to the column, and eluted therethrough with 1M aqueous acetic acid at 0.2 ml/min.

A sample of 5 ml of the dialyzed liquid from the dialysis sack was then added to the column and eluted with 1M aqueous acetic acid at 0.2 ml/min, with eluate monitoring at 280 nm. Fractions were collected every minute, lyophilized and numbered.

Identification of the Cytostatically Active Fractions

Each fraction was reconstituted in 110 μl of Dulbecco's modified Eagle's medium (DMEM) with fetal calf serum (FCS) 5 vol. %, 100 I.U. pencillin, 100 μg streptomycin and 2 nmole glutamine.

Malignant melanoma A375 cells (obtained from the American Type Culture Collection, Rockville, Md.) were counted in a counter (obtained from Coulter Diagnostics, Hialeah, Fla.), and about 4,000 cells were seeded into each well of a 96 well microtiter plate (obtained from Fisher Scientific, Springfield, N.J.) with 200 I.U. penicillin, 200 μg streptomycin and DMEM containing FCS 5 vol. %, 2 nmole glutamine, and 25 nM HEPES (hydroxyethylpiperazineethanesulfonic acid buffer) as needed to give a final well volume of 220 μl. Following a four-day incubation period at 36.5° C., the overlying medium of the cell cultures, except for one set designated as controls, were aspirated and replaced with 110 μl of the reconstituted venom fractions. Each culture was then pulsed with 0.5 μCi $^3$[H]-thymidine and incubated another 24 hours.

In addition to the previously mentioned controls, three additional sets of controls were established. One set of cultures was incubated without any venom fraction added thereto to insure that the medium change did not affect the cell growth. Another set of cultures contained an additional 24 μl fresh fetal calf serum. Still another set of cultures was incubated by adding 110 μl venom fraction diluant (the DMEM/FCS/penicillin/-streptomycin/glutamine mixture). All cultures, including controls were done in triplicate.

The cell cultures were terminated and harvested with a cell harvester (obtained from Flow Laboratories, McLean, Va., under the designation Titertek), removing the contents of each microtiter plate well onto glass fiber filter paper. The filter papers were air dried and cut into strips. The strips were placed in scintillation vials and counted in 2 ml scintillation solution (obtained from Fisher Scientific, Springfield , N.J., under the designation Scintiverse) using a scintillation counter (Model No. LS 100 C, obtained from Beckman Instruments, Somerset, N.J.) to determine the uptake of $^3$[H]-thymidine into newly synthesized DNA.

The venom fraction 18 fractions past the Bovine insulin marker (6000 daltons) showed 95% less $^3$[H]-thymidine incorporation than controls, indicating the presence of a peptide with a molecular weight less than 6000 daltons and with substantial cytostatic activity against malignant melanoma cells. Cells so treated are substantially less attenuated and more spheroid than control cells, further indicating the potent cytostatic activity of the fraction and possibly a permanent transformation to normal cytomorphology. A fraction obtained just ahead of the cytochrome C marker (12,5000 daltons) and estimated to have a molecular weight of about 15,000 showed similar cytostatic activity, indicating a larger precursor peptide or a tetramer. The remaining fractions were either cytotoxic or exhibited insignificant cytostatic activity.

Purification of the Cytostatically Active Peptide

The active low molecular weight fraction was bracketed with material from adjacent fractions, pooled, lyophilized, and resuspended in 0.04 wt. % aqueous trifluoroacetic acid at a pH of 2. A 500 μl sample was injected into a high pressure liquid chromatographic column (obtained from Waters Associates, Houston, Tex., under the designation μ-bonde-pak C18) and eluted in 0.04 wt. % aqueous trifluoroacetic acid at 1.2 ml/min, graded with 0-60 wt. % acetonitrile over 1 hour. The eluate was spectrophotometrically monitored at 280 nm, and fractions were collected every minute. The chromatogram is seen in FIG. 1, and 26 fractions in the range of the sample were demonstrated. These correspond to the chromatogram peaks labelled A through Z.

The HPLC fractions were cultured with the A375 cells and assayed as described above in connection with the gel filtration chromatography fractions. The fraction corresponding to peak Q was identified as the fraction containing the cytostatically active peptide, although there was some loss of activity (about 50% less $^3$[H]-thymidine uptake than controls). The peak Q fraction was rerun on the HPLC to insure homogeniety, and the chromatrogram is seen in FIG. 2. Additional material from the same fractions of the gel filtration material was run through the HPLC column as before, and material corresponding to peak Q was collected.

Analysis of the Cytostatically Active Peptide

The peak Q material was estimated to have a molecular weight in the vicinity of 3000 daltons by virtue of its gel filtration elution times relative to Bovine insulin. A 3 μg sample, or about 1 nmole, was analyzed for amino acid composition, and the results are seen in Table I.

TABLE I

| Amino Acid | nmole in 3 μg sample |
|---|---|
| Alanine | 0.5 |
| Arginine | 13.1 |
| Aspartic Acid | 3.9 |
| Cysteine | 7.9 |
| Glutamic Acid | 21.5 |
| Glycine | 20.0 |
| Isoleucine | 5.2 |
| Leucine | 14.1 |
| Lysine | 9.0 |
| Phenylalanine | 5.9 |
| Proline | 6.5 |
| Serine | 8.4 |
| Threonine | 3.0 |
| Valine | 0.4 |

The amino acid sequence of the peptide was then determined. A 4 μg sample of the peak Q fraction was digested with tosylamidophenylethyl chloromethyl ketone-treated trypsin at a substrate to enzyme weight ratio of 30:1 in 50 μl of 0.2M aqueous ammonium bicarbonate containing about 10 μg dithiothreitol for 12 hours. The digestion mixture was then applied to a HPLC column (Brownlee Aquapore C-8), and the fragments resolved in a trifluoroactetic acid/graded acetonitrile solvent system. Fragments were selected for sequence analysis with a gas phase protein sequencer (Model No. 470A, Applied Biosystems, Foster City, Calif. The partial sequence Phe-Cys-Arg-Phe-Leu-Leu- Cyr-Pro-Ser-Arg-Thr-Ser-Asp and a blocked amino terminus were determined.

The foregoing description of the invention is illustratory and explanatory thereof, and many variations will occur to those in the art. It is intended that all such variations within the scope and spirit of the appended claims be embraced thereby.

I claim:

1. A cell growth inhibitor, consisting essentially of:
   a fraction of venom, venom secretory epithelia, or a combination of venom and said epithelia, from a species of proteroglyphodont venomous snake, said fraction being substantially free of toxic substances occurring in said venom and said epithelia, said fraction containing a peptide exhibiting substantial activity as a cell growth inhibitor;
   said peptide containing an amino acid sequence of phenylalanine-cysteine-arginine-phenylalanine-leucine-leucine-cysteine-proline-serine-arginine-threonine-serine-aspartic acid;
   said fraction obtained by a process including the steps of: (a) dissolving said venom, said epithelia, or said combination thereof in an acidic medium; (b) heating said solution to a temperature and for a period of time sufficient to substantially react heat sensitive substances therein; (c) centrifuging said heated solution; (d) recovering supernatant liquid from said centrifuged solution; (e) dialyzing said supernatant liquid to substantially remove substances with a molecular weight below about 1000 daltons, (f) eluting said dialyzed liquid through a gel filtration chromatographic column with an acidic solvent, and (g) collecting said peptide-containing fraction as an eluate from said column.

2. The cell growth inhibitor of claim 1, wherein said species is *Crotalus atrox*.

3. The cell growth inhibitor of claim 1, wherein said process further includes purifying said collected eluate by high pressure liquid chromatography.

4. The cell growth inhibitor of claim 1, wherein said peptide contains about 27-29 amino acid groups and a blocked amino terminus, and has a molecular weight of about 3200-3500 daltons.

5. The cell growth inhibitor of claim 4, wherein said collected eluate consists essentially of substances having a molecular weight of about 3200-3500 daltons.

6. The cell growth inhibitor of claim 1, wherein said peptide is a precursor or oligomer of a 3200-3500 daltons molecular weight peptide which contains about 27-29 amino acid groups.

7. The cell growth inhibitor of claim 6, wherein said collected eluate consists essentially of substances having a molecular weight of about 15,000 daltons.

8. A cell growth inhibitor, consisting essentially of:
   a fraction of venom, venom secretory epithelia, or a combination of venom and said epithelia, from a species of proteroglyphodont venomous snake, said fraction being substantially free of toxic substances occurring in said venom and said epithelia, said fraction containing a peptide exhibiting substantial activity as a cell growth inhibitor;
   said fraction obtained by separating an acid-soluble, heat stable portion from said venom, said epithelia or said combination thereof, and separating said peptide-containing fraction from said acid-soluble portion by dialysis, gel filtration chromatography, electrophoresis, electrofocusing, high pressure liquid chromatography, ion exchange chromatography, or a combination thereof;
   said peptide having, or being a precursor or oligomer of peptide having, a molecular weight of about 3200-3500 daltons containing about 27-29 amino acid groups, said amino acids being selected from the group consisting of alanine, arginine, aspartic acid, cysteine, glutamic acid, glycine, isoleucine, leucine, lysine, phenylalanine, proline, serine, threonine, and valine, said amino acids forming a partial sequence of phenylalanine-cysteine-arginine-phenylalanine-leucine-leucine-cysteine-proline-serine-arginine-threonine-serine-aspartic acid and having a blocked amino terminus.

9. The cell growth inhibitor of claim 8, wherein said separation of said acid-soluble portion includes:
   dissolving said venom, said epithelia or said combination thereof in an acidic medium;
   heating said solution to a temperature and for a period of time sufficient to substantially react heat sensitive substances therein;
   centrifuging said heated solution; and
   recovering supernatant liquid from said centrifuged solution.

10. The cell growth inhibitor of claim 8, wherein said species is *Crotalus atrox*.

11. The cell growth inhibitor of claim 8, wherein said separation of said peptide-containing fraction includes:
    dialyzing said acid-soluble portion to subtantially remove substances with a molecular weight below about 1000 daltons;
    eluting said dialyzed portion through a gel filtration chromatographic column with an acidic solvent; and
    collecting said peptide-containing fraction as an eluate from said column.

12. The cell growth inhibitor of claim 11, wherein said collected eluate consists essentially of about 3200-3500 daltons molecular weight substances.

13. The cell growth inhibitor of claim 11, wherein said collected eluate consists essentially of about 15,000 daltons molecular weight substances.

14. The cell growth inhibitor of claim 11, wherein said separation of said peptide-containing fraction further includes:
    purifying said collected eluate by high pressure liquid chromatography with an acidic acetonitrile-graded solution.

15. A cell growth inhibitor, consisting essentially of:
    a cytostatically active peptide having a molecular weight of about 3200-3500 daltons, comprising about 27-29 amino acid groups containing at least the sequence phenylalanine-cysteine-arginine-phenylalanine-leucine-leucine-cysteine-proline-serine-arginine-threonine-serine-aspartic acid, and having a characteristic amino acid compositional analysis of alanine (0.5), arginine (13.1), aspartic acid (3.9), cysteine (7.9), glutamic acid (21.5), glycine (20.0), isoleucine (5.2), leucine (14.1), lysine (9.0), phenylalanine (5.9), proline (6.5), serine (8.4), threonine (3.0) and valine (0.4), wherein approximate molar proportions thereof are parenthetically indicated, said peptide being substantially free of cytotoxins.

16. The cell growth inhibitor of claim 15, wherein said peptide is a fraction of venom, venom secretory epithelia, or a combination of venom and said epithelia from a species of proteroglyphodont venomous snake.

17. The cell growth inhibitor of claim 3, wherein said species is *Crotalus atrox*.

* * * * *